(12) United States Patent
Roelle et al.

(10) Patent No.: US 8,222,314 B2
(45) Date of Patent: Jul. 17, 2012

(54) PHENYL ISOCYANATE-BASED URETHANE ACRYLATES, PROCESSES FOR PRODUCING AND METHODS OF USING THE SAME

(75) Inventors: Thomas Roelle, Leverkusen (DE);
Friedrich-Karl Bruder, Krefeld (DE);
Thomas Fäcke, Leverkusen (DE);
Marc-Stephan Weiser, Leverkusen (DE); Dennis Hönel, Zülpich (DE)

(73) Assignee: Bayer MaterialScience AG, Leverkusen (DE)

( * ) Notice: Subject to any disclaimer, the term of this patent is extended or adjusted under 35 U.S.C. 154(b) by 369 days.

(21) Appl. No.: 12/537,371

(22) Filed: Aug. 7, 2009

(65) Prior Publication Data

US 2010/0036013 A1    Feb. 11, 2010

(30) Foreign Application Priority Data

Aug. 8, 2008   (EP) .................................... 08014170

(51) Int. Cl.
*C08F 12/16* (2006.01)
*C08F 12/18* (2006.01)
*C08F 12/30* (2006.01)
*C07C 269/02* (2006.01)
*C07C 271/28* (2006.01)

(52) U.S. Cl. ............ 522/174; 359/3; 359/642; 359/838; 359/870; 359/885; 526/301; 560/9; 560/24; 560/29; 560/30; 560/33

(58) Field of Classification Search .............. 359/3, 642, 359/838, 870, 885; 522/174; 526/301; 560/9, 560/24, 29, 30, 33
See application file for complete search history.

(56) References Cited

U.S. PATENT DOCUMENTS

| | | | | |
|---|---|---|---|---|
| 5,342,891 | A * | 8/1994 | Koleske et al. | 525/162 |
| 5,916,987 | A | 6/1999 | Kobayashi et al. | |
| 6,780,546 | B2 | 8/2004 | Trentler et al. | |
| 6,794,471 | B2 | 9/2004 | Ohkuma et al. | |
| 7,338,984 | B2 | 3/2008 | Nakayama et al. | |
| 7,498,394 | B2 * | 3/2009 | Bowman et al. | 526/301 |
| 7,981,987 | B2 * | 7/2011 | Stockel et al. | 526/301 |
| 2002/0176169 | A1 | 11/2002 | Shoshi et al. | |

FOREIGN PATENT DOCUMENTS

| | | |
|---|---|---|
| DE | 2217744 A1 | 10/1973 |
| EP | 0810210 A2 | 12/1997 |
| EP | 0964019 A1 | 12/1999 |
| WO | WO-2004/009659 A1 | 1/2004 |
| WO | WO-2008/125199 A1 | 10/2008 |

OTHER PUBLICATIONS

Beckel, et al., Effect of "Effect of Aryl Substituents on the Reactivity of Phenyl Carbamate Acrylate Monomers" *Macromolecules*, 2004, vol. 37, pp. 4062-4069.
Beckel, et al., "Effect of Aliphatic Spacer Substitution on the Reactivity of Phenyl Carbamate Acrylate Monomers," *Macromolecules*, 2005, vol. 38, pp. 3093-3098.
Kilambi, et al., "Influence of molecular dipole on monoacrylate monomer reactivity," *Polymer* (2005), vol. 46, pp. 4735-4742.

* cited by examiner

*Primary Examiner* — Rabon Sergent
(74) *Attorney, Agent, or Firm* — Connolly Bove Lodge & Hutz LLP

(57) ABSTRACT

Urethane acrylates of the general Formula (I), corresponding salts, solvates or solvates of a salt thereof:

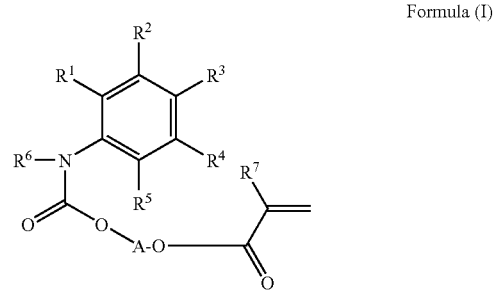

Formula (I)

wherein $R^1$, $R^2$, $R^3$, $R^4$ and $R^5$ each independently represent a substituent selected from the group consisting of hydrogen, halogens, $C_{1-6}$-alkyls, trifluoromethyl, $C_{1-6}$-alkylthios, $C_{1-6}$-alkylselenos, $C_{1-6}$-alkyltelluros, and nitro groups, with the proviso that at least one of $R^1$, $R^2$, $R^3$, $R^4$ and $R^5$ is not hydrogen; $R^6$ and $R^7$ each independently represent a substituent selected from the group consisting of hydrogen and $C_{1-6}$-alkyls; and A represents a saturated or unsaturated or linear or branched $C_{1-6}$-alkyl radical or a polyalkylene oxide radical having 2-6 ethylene oxide or propylene oxide units; processes for producing and methods of using the same.

13 Claims, 1 Drawing Sheet

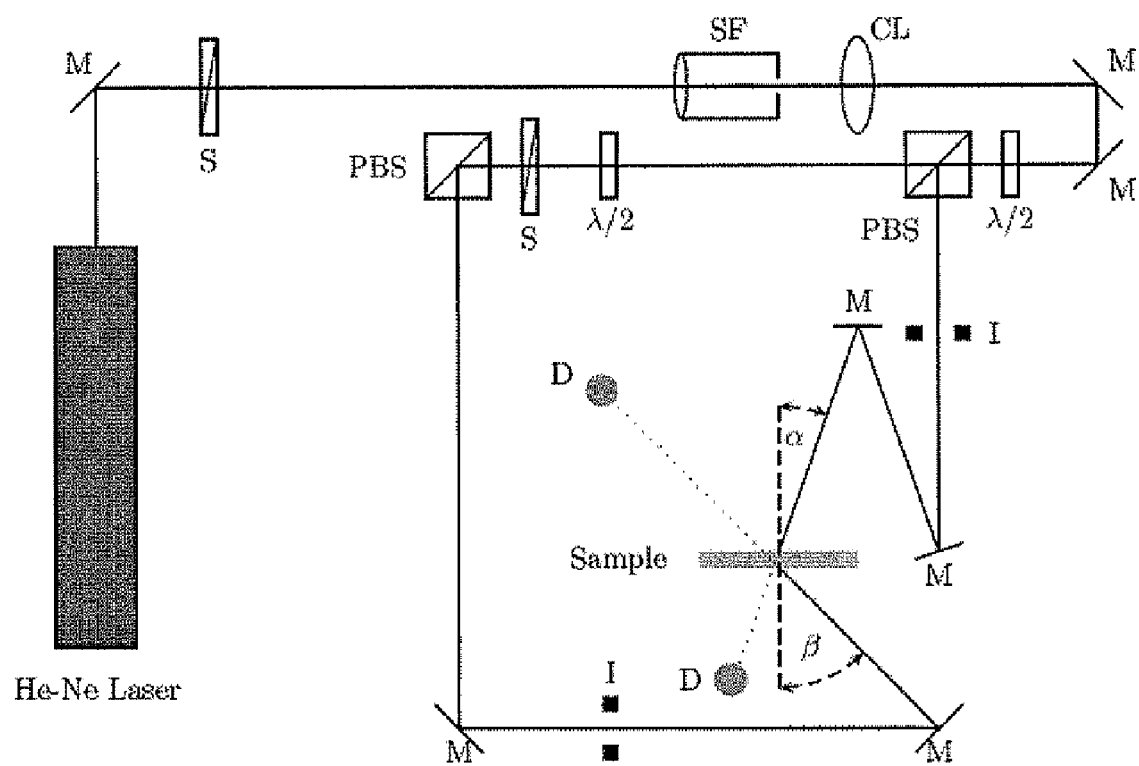

PHENYL ISOCYANATE-BASED URETHANE ACRYLATES, PROCESSES FOR PRODUCING AND METHODS OF USING THE SAME

BACKGROUND OF THE INVENTION

Coatings having a high refractive index (n) are known from various applications, for example, optical lenses, antireflection coatings, planar waveguides or holographically writeable films. Coatings having high refractive indices can in principle be produced by various methods. By a purely physical route, metal oxides having a high refractive index, such as, for example, $TiO_2$, $Ta_2O_5$, $CeO_2$, $Y_2O_3$, are deposited in a high vacuum via plasma methods in the so-called "sputter process." While refractive indices of more than 2.0 in the visible wavelength range can be achieved thereby without problems, the process is relatively complicated and expensive.

EP 0964019 A1 and WO 2004/009659 A1, for example, disclose organic polymers, for example, sulfur-containing polymers or halogenated acrylates (tetrabromophenyl acrylate, Polyscience Inc.), which inherently have a higher refractive index than conventional polymers and which can be applied to surfaces by simple methods from organic solutions according to conventional coating processes. However, the refractive indices are generally limited here to values up to about 1.7, measured in the visible wavelength range.

A further process variant which is becoming increasingly important is based on metal oxide nanoparticles, which are incorporated into organic or polymeric binder systems. The corresponding nanoparticle-polymer hybrid formulations can be applied to various substrates in a simple and economical manner, for example by means of spin coating. The achievable refractive indices are usually between the first-mentioned sputter surfaces and the layers of polymers having a high refractive index. With increasing nanoparticle contents, it is possible to achieve increasing refractive indices. For example, U.S. Pat. App. Pub. No. 2002/0176169 A1 discloses the preparation of nanoparticle-acrylate hybrid systems, the layers having a high refractive index containing a metal oxide, such as, for example, titanium oxide, indium oxide or tin oxide, and a UV-crosslinkable binder, for example based on acrylate, in an organic solvent. After spin coating, evaporation of the solvent and UV irradiation, corresponding coatings having a real part n of the refractive index of 1.60 to 1.95, measured in the visible wavelength range, can be obtained.

In addition to the physical properties, however, the processability and compatibility with other components are also important. Thus, organic materials which are obtained by photopolymerization, generally as homo- or copolymers of monomers having a high refractive index, play an important role, for example for the production of optical components, such as lenses, prisms and optical coatings (see, e.g., U.S. Pat. No. 5,916,987), or for the production of a contrast in holographic materials (see, e.g., U.S. Pat. No. 6,780,546). For such and similar applications, there is a need to be able to adjust the refractive index in a targeted manner and to vary it over ranges, for example by admixing components having a high refractive index.

For the abovementioned fields of use, polymers of olefinically unsaturated compounds, such as, preferably, (meth)acrylates, are typically used. In order to achieve a refractive index of 1.5 or higher, halogen-substituted aromatic (meth)acrylates or special alkyl methacrylates described in U.S. Pat. No. 6,794,471 can be used. Owing to their complicated preparation, the latter in particular are disadvantageous.

The suitability of substituted phenyl isocyanate-based urethane acrylates for the preparation of corresponding polymers has been described by Bowman (Polymer 2005, 46, 4735-4742).

The unpublished International Application PCT/EP2008/002464 discloses (meth)acrylates having a refractive index at $\lambda = 532$ nm of at least 1.5, which are suitable for the production of optical data media, in particular those for holographic storage methods, and are based on industrially available raw materials. In this context, phenyl isocyanate-based compounds are also known, these always being based on unsubstituted phenyl rings on the isocyanate side.

In photopolymer formulations, acrylates having a high refractive index play a decisive role as a contrast-imparting component (U.S. Pat. No. 6,780,546). The interference field of signal and reference lightbeam (two planar waves in the simplest case) is mapped into a refractive index grating, which contains all information of the signal (the hologram), by the local photopolymerization at locations of high intensity in the interference field by the acrylates having a high refractive index. By illuminating the hologram only with the reference lightbeam, the signal can then be reconstructed. The strength of the signal thus reconstructed in relation to the strength of the incident reference light is referred to as diffraction efficiency, or DE below. In the simplest case of a hologram which is formed by the superposition of two planar waves, the DE is obtained from the quotient of the intensity of the light diffracted on reconstruction and the sum of the intensities of incident reference light and diffracted light. The higher the DE, the more efficient is a hologram with respect to the necessary quantity of reference light which is necessary in order to visualize the signal with a fixed brightness. Acrylates having a high refractive index are capable of producing refractive index gratings having a high amplitude between regions with the lowest refractive index and regions with the highest refractive index and thereby of permitting holograms having a high DE in photopolymer formulations

BRIEF SUMMARY OF THE INVENTION

The present invention relates, in general, to novel specially substituted phenyl isocyanate-based urethane acrylates having a high refractive index and to a process for the preparation thereof and the use thereof.

It has been surprisingly found that special substituted phenyl isocyanate-based urethane acrylates can be cured to give coatings and moldings having particularly high refractive indices in combination with improved DE values and are therefore particularly suitable as starting material for the production of materials having a high refractive index, in particular optical lenses, antireflection coatings, planar waveguides or holographically writeable materials.

The present invention therefore relates to urethane acrylates of the general Formula (I)

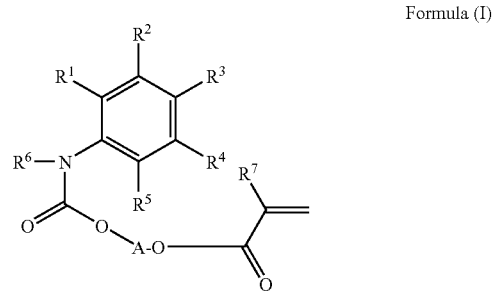

Formula (I)

in which $R^1$, $R^2$, $R^3$, $R^4$, $R^5$, in each case by themselves, may be a hydrogen or halogen atom or a $(C_1$-$C_6)$-alkyl, trifluoromethyl, $(C_1$-$C_6)$-alkylthio, $(C_1$-$C_6)$-alkylseleno, $(C_1$-$C_6)$-alkyltelluro or nitro group, with the proviso that at least one substituent of the group $R^1$, $R^2$, $R^3$, $R^4$, $R^5$ is not hydrogen $R^6$, $R^7$, in each case by themselves, may be hydrogen or a $(C_1\text{-}C_6)$-alkyl group and A is a saturated or unsaturated or linear or branched $(C_1\text{-}C_6)$-alkyl radical or a polyethylene oxide (m=2-6) or polypropylene oxide (m=2-6) radical, the corresponding salts, solvates or solvates of the salts of the compounds according to Formula (I) also being included.

One embodiment of the present invention includes a urethane acrylate of the general Formula (I), a corresponding salt, a solvate or a solvate of a salt thereof:

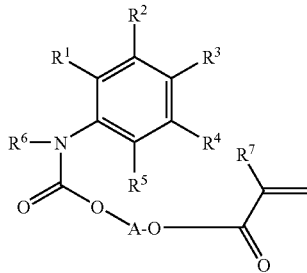

Formula (I)

wherein $R^1$, $R^2$, $R^3$, $R^4$ and $R^5$ each independently represent a substituent selected from the group consisting of hydrogen, halogens, $C_{1\text{-}6}$-alkyls, trifluoromethyl, $C_{1\text{-}6}$-alkylthios, $C_{1\text{-}6}$-alkylselenos, $C_{1\text{-}6}$-alkyltelluros, and nitro groups, with the proviso that at least one of $R^1$, $R^2$, $R^3$, $R^4$ and $R^5$ is not hydrogen; $R^6$ and $R^7$ each independently represent a substituent selected from the group consisting of hydrogen and $C_{1\text{-}6}$-alkyls; and A represents a saturated or unsaturated or linear or branched $C_{1\text{-}6}$-alkyl radical or a polyalkylene oxide radical having 2-6 ethylene oxide or propylene oxide units.

Another embodiment of the present invention includes layers, layered structures and/or moldings comprising a urethane acrylate according to the various embodiments of the invention.

Yet another embodiment of the invention includes articles such as, for example, optical lenses, mirrors, deflection mirrors, filters, diffusion screens, diffraction elements, waveguides, light guides, projection screens, masks, personal portraits, biometric presentations in security documents, images, image structures and combinations thereof which comprise a layer or molding according to the present invention.

Preferred radicals $R^1$ to $R^5$ are $(C_1\text{-}C_6)$-alkylthio substituents or chlorine or bromine, and methylthio substituents or chlorine or bromine are particularly preferred. In a particularly preferred embodiment, at least one substituent of the group $R^1$, $R^2$, $R^3$, $R^4$ and $R^5$ is a $(C_1\text{-}C_6)$-alkylthio substituent or chlorine or bromine and the other substituents of the group $R^1$, $R^2$, $R^3$, $R^4$ and $R^5$ are hydrogen atoms. Preferred radicals $R^6$ and $R^7$ are hydrogen atoms. The radical A is preferably a linear $C_2\text{-}C_4$ or branched $C_3$-alkyl radical, particularly preferably a linear $C_2$— or $C_4$-alkyl radical.

The urethane acrylates of the present invention are obtainable by reacting isocyanates of the Formula (II)

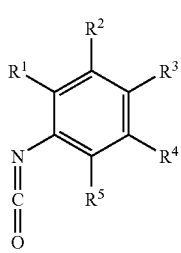

Formula (II)

with isocyanate-reactive compounds of the Formula (III)

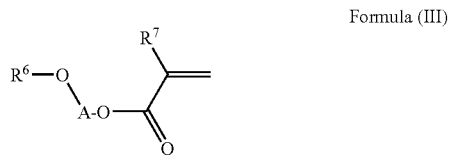

Formula (III)

the radicals having the abovementioned meaning.

BRIEF DESCRIPTION OF THE SEVERAL VIEWS OF THE DRAWING

The foregoing summary, as well as the following detailed description of the invention, may be better understood when read in conjunction with the appended drawings. For the purpose of assisting in the explanation of the invention, there are shown in the drawings representative embodiments which are considered illustrative. It should be understood, however, that the invention is not limited in any manner to the precise arrangements and instrumentalities shown.

In the drawings:

FIG. 1 is schematic representation of a holographic measuring arrangement used in the Examples described herein.

DETAILED DESCRIPTION OF THE INVENTION

As used herein, the singular terms "a" and "the" are synonymous and used interchangeably with "one or more" and "at least one," unless the language and/or context clearly indicates otherwise. Accordingly, for example, reference to "a urethane acrylate" herein or in the appended claims can refer to a single urethane acrylate or more than one urethane acrylate. Additionally, all numerical values, unless otherwise specifically noted, are understood to be modified by the word "about."

Examples of compounds of the Formula (IS) are 2-thiomethylphenyl isocyanate, 3-thiomethylphenyl isocyanate, 4-thiomethylphenyl isocyanate, 2-chlorophenyl isocyanate, 3-chlorophenyl isocyanate, 4-chlorophenyl isocyanate, 2-bromophenyl isocyanate, 3-bromophenylisocyanate, 4-bromophenyl isocyanate, 2-iodophenyl isocyanate, 3-iodophenyl isocyanate, 4-iodophenyl isocyanate or mixtures thereof.

2-thiomethylphenyl isocyanate, 3-thiomethylphenyl isocyanate, 4-thiomethylphenyl isocyanate, 2-chlorophenyl isocyanate, 3-chlorophenyl isocyanate, 4-chlorophenyl isocyanate, 2-bromophenyl isocyanate, 3-bromophenyl isocyanate, 4-bromophenyl isocyanate or mixtures thereof are preferred.

2-thiomethylphenyl isocyanate, 3-thiomethylphenyl isocyanate and 4-thiomethylphenyl isocyanate, 3-chlorophenyl isocyanate, 3-bromophenyl isocyanate or mixtures thereof are particularly preferred.

Compounds of the Formula (III) which may be used are, for example, 2-hydroxyethyl(meth)acrylate, polyethylene oxide mono(meth)acrylate, polypropylene oxide mono(meth)acrylates, polyalkylene oxide mono(meth)acrylates, 2-hydroxypropyl(meth)acrylate, 3-hydroxypropyl acrylate, 4-hydroxybutyl(meth)acrylate, 3-hydroxy-2,2-dimethylpropyl(meth)acrylate, hydroxypropyl(meth)acrylate or mixtures thereof.

2-hydroxyethyl acrylate, 2-hydroxypropyl acrylate, 3-hydroxypropyl acrylate, 4-hydroxybutyl acrylate, polypropylene oxide mono(meth)acrylates, polyethylene oxide mono(meth)acrylates or mixtures thereof are preferred.

2-hydroxyethyl acrylate, 2-hydroxypropyl acrylate, 3-hydroxypropyl acrylate and 4-hydroxybutyl acrylate or mixtures thereof are particularly preferred.

The reaction of compounds of the Formula (II) with compounds of the Formula (III) is a urethanization. The reaction of compounds of the Formula (II) with compounds of the Formula (III) can be effected with the aid of the catalysts known for accelerating isocyanate addition reactions, such as, for example, tertiary amines, tin, zinc, iron or bismuth compounds, in particular triethylamine, 1,4-diazabicyclo[2.2.2]octane, bismuth octanoate or dibutyltin dilaurate, which can be initially introduced concomitantly or metered in later. The urethane acrylates according to the invention have a content of less than 0.5% by weight, preferably less than 0.2% by weight, particularly preferably less than 0.1% by weight, based on the urethane acrylate, of isocyanate groups (M=42) or free residual monomers. Furthermore, the urethane acrylates according to the invention contain contents of less than 1% by weight, preferably less than 0.5% by weight and particularly preferably less than 0.2% by weight, based on the urethane acrylate, of unreacted component compounds of the Formula (III). In the preparation of the urethane acrylates according to the invention, the compounds of the Formula (II) and the compounds of the Formula (III) can be dissolved in an unreactive solvent, for example an aromatic or aliphatic hydrocarbon or an aromatic or aliphatic halogenated hydrocarbon, or a coating solvent, such as, for example, ethyl acetate or butyl acetate or acetone or butanone or an ether, such as tetrahydrofuran or tert-butyl methyl ether, or a dipolar aprotic solvent, such as dimethylsulphoxide or N-methylpyrrolidone or N-ethylpyrrolidone, and initially introduced or metered in in a manner familiar to a person skilled in the art. After the end of the reaction, the unreactive solvent is removed from the mixture under atmospheric pressure or under reduced pressure and the end point is determined by determining the solids content. The solids contents are typically in a range from 99.999 to 95.0% by weight, preferably from 99.998 to 98.0% by weight, based on the urethane acrylate.

The urethane acrylates according to the invention can furthermore be protected from undesired polymerization by the addition of stabilizers. Such stabilizers may be oxygen-containing gas, as well as chemical stabilizers as described, for example, in Houben-Weyl, Methoden der organischen Chemie [Methods of Organic Chemistry], 4th edition, volume XIV/1, Georg Thieme Verlag, Stuttgart 1961, page 433 et seq. The following may be mentioned as examples: sodium dithionite, sodium hydrogen sulphide, sulphur, hydrazine, phenylhydrazine, hydrazobenzene, N-phenyl-β-naphthylamine, N-phenylethanoldiamine, dinitrobenzene, picric acid, p-nitrosodimethylaniline, diphenylnitrosamine, phenols, such as para-methoxyphenol, 2,5-di-tert-butylhydroquinone, 2,6-di-tert-butyl-4-methylphenol, p-tert-butylpyrocatechol or 2,5-di-tert-amylhydroquinone, tetramethylthiuram disulphide, 2-mercaptobenzothiazole, dimethyldithiocarbamic acid sodium salt, phenothiazine, N-oxyl compounds, such as, for example, 2,2,6,6-tetramethylpiperidine N-oxide (TEMPO) or one of its derivatives. 2,6-di-tert-butyl-4-methylphenol and para-methoxyphenol and mixtures thereof are preferred. Such stabilizers are typically used in an amount of 0.001 to 1% by weight, preferably 0.01 to 0.5% by weight, based on the urethane acrylate to be stabilized.

Layers, layer structures and mouldings obtainable from the urethane acrylates of the Formula (I), according to the invention, typically have a refractive index of >1.50, preferably >1.55, particularly preferably >1.58, at 405 nm and therefore likewise form a subject of the invention.

Layers, layer structures and mouldings obtainable from formulations which contain the urethane acrylates of the Formula (I), according to the invention, furthermore typically have DE values, measured by means of two-beam interference in reflection arrangement, of >25%, preferably >30%, particularly preferably >40%, very particularly preferably >50%. The exact description of the method is contained in the example section of the application.

The urethane acrylates of the Formula (I), according to the invention, are therefore outstandingly suitable for the production of holographic media and holographic photopolymer films.

The invention therefore also relates to a process for exposing holographic media and holographic photopolymer films to light, in which the urethane acrylates according to the invention, which are present in a polymer matrix, are selectively polymerized by electromagnetic radiation.

After appropriate holographic exposure to light, such holographic media are suitable for the production of holographic optical elements which have, for example, the function of an optical lens, a mirror, a deflection mirror, a filter, a diffusion screen, a diffraction element, a waveguide, a light guide, a projection screen and/or a mask.

Moreover, holographic images or presentations can also be produced therewith, such as, for example, for personal portraits, biometric presentations in security documents, or generally of images or image structures for advertising, security labels, trademark protection, trademark branding, labels, design elements, decorations, illustrations, trading cards, images and the like and images which can represent digital data, inter alia also in combination with the products described above.

The invention will now be described in further detail with reference to the following non-limiting examples.

EXAMPLES

Unless noted otherwise, all percentage data are based on percent by weight.

The measurement of the refractive index was effected at a wavelength of 405 n. The refractive index n as a function of the wavelength of the samples were obtained from the transmission and reflection spectra. For this purpose, about 100-300 nm thick films of the samples were applied by spin coating to quartz glass substrates from dilute solution in butyl acetate. The transmission and reflection spectrum of this layer packet was measured with a spectrometer from STEAG ETA Optik, CD-Measurement System ETA-RT, and the layer thickness and the spectral curve of n were then adapted to the measured transmission and reflection spectra. This is effected using the internal software of the spectrometer and additionally requires the n data of the quartz glass substrate which were determined beforehand in a blank measurement.

Example 1

2-({[3-(Methylsulphanyl)phenyl]carbamoyl}oxy) ethyl prop-2-enoate 0.02 g of 2,6-di-tert-butyl-4-methylphenol, 0.01 g of Desmorapid Z, 11.7 g of 3-(methylthio)phenyl isocyanate were initially introduced into a 100 ml round-bottomed flask and heated to 60° C. Thereafter, 8.2 g of 2-hydroxyethyl acrylate were added dropwise and the mixture was kept farther at 60°

C. until the isocyanate content had fallen below 0.1%. Cooling was then effected. The product was obtained as a light yellow liquid.

Example 2

2-({[3-(Methylsulphanyl)phenyl]carbamoyl}oxy) propyl prop-2-enoate 0.05 g of 2,6-di-tert-butyl-4-methylphenol, 0.02 g of Desmorapid Z, 26.8 g of 3-(methylthio)phenyl isocyanate in 50 g of ethyl acetate were initially introduced into a 250 ml round-bottomed flask and heated to 60° C. Thereafter 21.1 g of 2-hydroxypropyl acrylate were added dropwise and the mixture was kept further at 60° C. until the isocyanate content had fallen below 0.1%. Thereafter, the ethyl acetate was distilled off at 5 mbar and cooling was effected. The product was obtained as a light yellow liquid.

Example 3

2-({[3-(Methylsulphanyl)phenyl]carbamoyl}oxy) butyl prop-2-enoate 0.05 g of 2,6-di-tert-butyl-4-methylphenol, 0.02 g of Desmorapid Z, 26.7 g of 3-(methylthio)phenyl isocyanate were initially introduced into a 250 ml round-bottomed flask and heated to 60° C. Thereafter, 23.3 g of 2-hydroxybutyl acrylate were added dropwise and the mixture was kept further at 60° C. until the isocyanate content had fallen below 0.1%. Thereafter, the ethyl acetate was distilled offat 5 mbar and cooling was effected. The product was obtained as a crystalline solid.

Example 4

2-{2-[2-({[3-(Methylsulphanyl)phenyl] carbamoyl}oxy)ethoxy]ethoxy}ethyl 2-methylprop-2-enoate 0.02 g of 2,6-di-tert-butyl-4-methylphenol, 0.01 g of Desmorapid Z, 8.6 g of 3-(methylthio)phenyl isocyanate were initially introduced into a 100 ml round-bottomed flask and heated to 60° C. Thereafter, 11.7 g of polyethylene glycol monomethacrylate (PEM3, from LAPORTE Performance Chemicals UK LTD) were added dropwise and the mixture was kept further at 60° C. until the isocyanate content had fallen below 0.1%. Cooling was then effected. The product was obtained as a light yellow liquid.

Example 5

19-{[3-(Methylsulphanyl)phenyl]amino}-19-oxo-3, 6,9,12,15,18-hexaoxanonadec-1-yl prop-2-enoate 0.02 g of 2,6-di-tert-butyl-4-methylphenol, 0.01 g of Desmorapid Z, 6.4 g of 3-(methylthio)phenyl isocyanate were initially introduced into a 100 ml round-bottomed flask and heated to 60° C. Thereafter, 13.6 g of Bisomer™ PEA 6 (from Cognis Deutschland GmbH & Co KG) were added dropwise and the mixture was kept further at 60° C. until the isocyanate content had fallen below 0.1%. Cooling was then effected. The product was obtained as a light yellow liquid.

Example 6

2,5,8,11,14,17-Hexamethyl-19-{[3-(methylsulphanyl)phenyl]amino}-19-oxo-3,6,9,12,15,18-hexaoxanonadec-1-yl prop-2-enoate 0.02 g of 2,6-di-tert-butyl-4-methylphenol, 0.01 g of Desmorapid 7, 5.6 g of 3-(methylthio)phenyl isocyanate were initially introduced into a 100 ml round-bottomed flask and heated to 60° C. Thereafter, 14.3 g of Bisomer™ PPA 6 (from Cognis Deutschland GmbH & Co KG) were added dropwise and the mixture was kept further at 60° C. until the isocyanate content had fallen below 0.1%. Cooling was then effected. The product was obtained as a crystalline solid.

Example 7

2-({[2-(Methylsulphanyl)phenyl]carbamoyl}oxy) propyl prop-2-enoate 0.008 g of 2,6-di-tert-butyl-4-methylphenol, 0.004 g of Desmorapid Z, 4.8 g of 2-(methylthio)phenyl isocyanate in 8.5 g of ethyl acetate were initially introduced into a 50 ml round-bottomed flask and heated to 60° C. Thereafter, 3.7 g of 3-hydroxypropyl acrylate were added dropwise and the mixture was kept further at 60° C. until the isocyanate content had fallen below 0.1%. Thereafter, the ethyl acetate was distilled off at 5 mbar and cooling was effected. The product was obtained as a light yellow liquid.

Example 8

2-({[2-(Methylsulphanyl)phenyl]carbamoyl}oxy) butyl prop-2-enoate 0.008 g of 2,6-di-tert-butyl-4-methylphenol, 0.004 g of Desmorapid Z, 4.3 g of 2-(methylthio)phenyl isocyanate in 8.5 g ethyl acetate were initially introduced into a 50 ml round-bottomed flask and heated to 60° C. Thereafter, 4 g of 3-hydroxybutyl acrylate were added dropwise and the mixture was kept further at 60° C. until the isocyanate content had fallen below 0.1%. Thereafter, the ethyl acetate was distilled off at 5 mbar and cooling was effected. The product was obtained as a light yellow liquid.

Example 9

2-({[4-(Methylsulphanyl)phenyl]carbamoyl}oxy) ethyl prop-2-enoate 0.02 g of 2,6-di-tert-butyl-4-methylphenol, 0.01 g of Desmorapid Z, 4.7 g of 4-(methylthio)phenyl isocyanate in 25 g of ethyl acetate were initially introduced into a 100 ml round-bottomed flask and heated to 60° C. Thereafter, 4.1 g of 2-hydroxyethyl acrylate were added dropwise and the mixture was kept further at 60° C. until the isocyanate content had fallen below 0.1%. Thereafter, the ethyl acetate was distilled off at 5 mbar and cooling was effected. The product was obtained as a crystalline solid.

Example 10

2-({[4-(Methylsulphanyl)phenyl]carbamoyl}oxy) propyl prop-2-enoate 0.02 g of 2,6-di-tert-butyl-4-methylphenol, 0.01 g of Desmorapid Z, 14.0 g of 4-(methylthio)phenyl isocyanate in 25 g of ethyl acetate were initially introduced into a 100 ml round-bottomed flask and heated to 60° C. Thereafter, 11.0 g of 3-hydroxypropyl acrylate were added dropwise and the mixture was kept further at 60° C. until the isocyanate content had fallen below 0.1%. Thereafter, the ethyl acetate was distilled off at 5 mbar and cooling was effected. The product was obtained as a light yellow liquid.

Example 11

2-({[4-(Methylsulphanyl)phenyl]carbamoyl}oxy)butyl prop-2-enoate 0.02 g of 2,6-di-tert-butyl-4-methylphenol, 0.01 g of Desmorapid Z, 13.3 g of 4-(methylthio)phenyl isocyanate in 25 g of ethyl acetate were initially introduced into a 100 ml round-bottomed flask and heated to 60° C. Thereafter, 11.6 g of 3-hydroxybutyl acrylate were added dropwise and the mixture was kept further at 60° C. until the isocyanate content had fallen below 0.1%. Thereafter, the ethyl acetate was distilled off at 5 mbar and cooling was effected. The product was obtained as a crystalline solid.

Example 12

2-{[(3-Chlorophenyl)carbamoyl]oxy}ethyl prop-2-enoate 0.15 g of 2,6-di-tert-butyl-4-methylphenol, 0.075 g of Desmorapid Z, 85.3 g of 3-chlorophenyl isocyanate were initially introduced into a 500 ml round-bottomed flask and heated to 60° C. Thereafter, 65.5 g of 3-hydroxybutyl acrylate were added dropwise and the mixture was kept further at 60° C. until the isocyanate content had fallen below 0.1%. Cooling was then effected. The product was obtained as a crystalline solid.

Example 13

2-{[(3-Bromophenyl)carbamoyl]oxy}ethyl prop-2-enoate 0.015 g of 2,6-di-tert.-butyl4-methylphenol, 0.007 g of Desmorapid Z, 9.4 g of 3-bromophenyl isocyanate were initially introduced in a 20 ml sample bottle and heated to 60° C. Thereafter, 5.5 g of 3-hydroxybutyl acrylate were added dropwise and the mixture was kept further at 60° C. until the isocyanate content had fallen below 0.1%. Cooling was then effected. The product was obtained as a crystalline solid.

Comparative Example 1

2-[(Phenylcarbamoyl)oxy]ethyl prop-2-enoate 0.25 g of 2,6-di-tert-butyl-4-methylphenol, 0.12 g of Desmorapid Z, 126.4 g of phenyl isocyanate were initially introduced into a 500 ml round-bottomed flask and heated to 60° C. Thereafter, 123.3 g of 2-hydroxyethyl acrylate were added dropwise and the mixture was kept further at 60° C. until the isocyanate content had fallen below 0.1%. Cooling was then effected. The product was obtained as a crystalline solid (preparation described in DE 2329142).

TABLE 1

Characterization of examples 1-13 and of comparative example 1

| Example | Refractive index at $\lambda$ = 405 nm | Double bond density eq/kg (SC) |
|---|---|---|
| 1 | 1.626 | 3.55 |
| 2 | 1.614 | 3.23 |
| 3 | 1.609 | 3.23 |
| 4 | 1.600 | 2.61 |
| 5 | 1.536 | 1.93 |
| 6 | 1.532 | 1.71 |
| 7 | 1.588 | 3.38 |
| 8 | 1.591 | 3.23 |
| 9 | 1.620 | 3.55 |
| 10 | 1.614 | 3.38 |
| 11 | n.b. | 3.23 |
| 12 | 1.589 | 3.72 |
| 13 | 1.602 | 3.19 |
| Comparative example 1 | 1.591 | 4.26 |

For testing the optical properties, media were produced and subjected to optical measurements as described below:
Preparation of the Polyol Component:

0.18 g of tin octanoate, 374.8 g of ε-caprolactone and 374.8 g of a difunctional polytetrahydrofuran polyether polyol (equivalent weight 500 g/mol OH) were initially introduced into a 1 l flask and heated to 120° C. and kept at this temperature until the solids content (proportion of nonvolatile constituents) was 99.5% by weight or more. Thereafter, cooling was effected and the product was obtained as a waxy solid.
Medium 1:

5.927 g of the polyol component prepared as described above were mixed with 2.50 g of urethane acrylate from Example 1, 0.10 g of CGI 909 (experimental product from. Ciba Inc, Basle, Switzerland) and 0.010 g of new methylene blue at 60° C. and 3.50 g of N-ethylpyrilidone so that a clear solution was obtained. Thereafter, cooling to 30° C. was effected, 1.098 g of Desmodur® XP 2410 (experimental product of Bayer MaterialScience AG, Leverkusen, Germany, hexane diisocyanate-based polyisocyanate, proportion of iminooxadiazinedione at least 30%, NCO content: 23.5%) were added and mixing was effected again. Finally, 0.006 g of Fomrez UL 28 (urethanization catalyst, commercial product from Momentive Performance Chemicals, Wilton, Conn., USA) was added and mixing was effected again briefly. The liquid material obtained was then poured onto a glass plate and covered there with a second glass plate which was kept at a distance of 20 µm by spacers. This test specimen was first left for 30 minutes at room temperature and then cured for two hours at 50° C.

The media 2-5 were produced in an analogous manner from the examples mentioned in Table 1.
Comparative Medium:

5.927 g of the polyol component prepared as described above were mixed with 2.50 g of 2-[(phenylcarbamoyl)oxy]ethyl prop-2-enoate (comparative Example 1), 0.10 g of CGI 909 (experimental product of Ciba Inc., Basle, Switzerland) and 0.010 g of new methylene blue at 60° C. and 3.50 g of N-ethylpyrilidone so that a clear solution was obtained. Thereafter, cooling to 30° C. was effected, 1.098 g of Desmodur® XP 2410 (experimental product of Bayer Material-Science AG, Leverkusen, Germany, hexane diisocyanate-based polyisocyanate, proportion of iminooxadiazinedione at least 30%, NCO content: 23.5%) were added and mixing was effected again. Finally, 0.006 g of Fomrez UL 28 (urethanization catalyst, commercial product of Momentive Performance Chemicals, Wilton, Conn., USA) was added and mixing was effected again briefly. The liquid material obtained was then poured onto a glass plate and covered there with a second glass plate which was kept at a distance of 20 µm by spacers. This test specimen was first left for 30 minutes at room temperature and then cured for two hours at 50° C.

Measurement of the Holographic Properties of the Media by Means of Two-Beam Interference in Reflection Arrangement:

The media produced as described were then tested with respect to their holographic properties by means of a measuring arrangement according to FIG. 1, as follows:

The beam of an He—Ne laser (emission wavelengths 633 nm) was converted with the aid of the spatial filter (SF) and together with the collimation lens (CL) into a parallel homogeneous beam. The final cross sections of the signal and reference beam are determined by the iris diaphragms (I). The diameter of the iris diaphragm opening is 0.4 cm. The polarization-dependent beam splitters (PBS) split the laserbeam into two coherent identically polarized beams. The power of the reference beam was adjusted to 0.5 mW and the power of the signal beam to 0.65 mW via the $\lambda/2$ plates. The powers were determined with the semiconductor detectors (D) after removal of the sample. The angle of incidence ($\alpha$) of the reference beam is 21.8° and the angle of incidence ($\beta$) of the signal beam is 41.8°. At the location of the sample (medium), the interference field of the two overlapping beams produced a grating of light and dark strips which are perpendicular to the angle bisector of the two beams incident on the sample (reflection hologram). The strip spacing in the medium is ~225 nm (refractive index of the medium assumed to be ~1.49).

Meaning of the Reference Numerals in FIG. 1:

M=mirror, S=shutter, SF=spatial filter, CL=collimator lens, $\lambda/2=\lambda/2$ plate, PBS=polarization-sensitive beam splitter, D=detector, I=iris diaphragm, $\alpha=21.80°$, $\beta=41.8°$.

Holograms were written into the medium in the following manner:

Both shutters (S) are opened for the exposure time t.

Thereafter, with shutters (S) closed, the medium was allowed a time of 5 minutes for the diffusion of the still unpolymerized writing monomers.

The holograms written were now read in the following manner. The shutter of the signal beam remained closed. The shutter of the reference beam was opened. The iris diaphragm of the reference beam was closed to a diameter of <1 mm. This ensured that the beam always lay completely in the hologram written beforehand for all angles ($\Omega$) of rotation of the medium. The turntable now covered the angular range of $\Omega=0°$ to $\Omega=20°$ with an angular step width of 0.05° under computer control. At each angle $\Omega$ reached, the powers of the beam transmitted in the zero order were measured by means of the corresponding detector D and the powers of the beam diffracted in the first order were measured by means of the detector D. At each angle $\Omega$ reached, the diffraction efficiency was obtained as the quotient of:

Power in the detector of the diffracted beam/(power in the detector of the diffracted beam+power in the detector of the transmitted beam)

The maximum diffraction efficiency (DE) of the hologram, i.e. its peak value, was determined. For this purpose, it might be necessary to change the position of the detector of the diffracted beam in order to determine this maximum value.

For a formulation, this procedure was if necessary repeated several times for different exposure times t on different media in order to determine the average energy dose of the incident laser beam during writing of the hologram DE at which the saturation value is reached. The average energy dose E is obtained as follows from the powers of the two partial beams (0.50 mW and 0.67 mW), the exposure time t and the diameter of the iris diaphragm (0.4 cm):

$$E(\text{mJ/cm}^2)=2\cdot[(0.50\text{ mW}+0.67\text{ mW})\cdot t(s)]/[\pi\cdot 0.4^2\text{ cm}^2]$$

The powers of the partial beams were adapted so that the same power density is achieved in the medium at the angles $\alpha$ and $\beta$ used.

The following measured values for DE [%] were obtained at the dose E [mJ/cm²]:

TABLE 2

Holographic evaluation of selected examples

| Medium | Example | Dose [mJ/cm²] | DE [%] |
|---|---|---|---|
| 1 | 1 | 37 | 68 |
| 2 | 5 | 37 | 26 |
| 3 | 7 | 73 | 26 |
| 4 | 8 | 73 | 57 |
| 5 | 13 | 73 | 38 |
| Comparative medium | Comparative example 1 | 73 | 24 |

The values found for the dynamic range (DE) show that the urethane acrylate used in the comparative medium is less suitable for use in holographic media, whereas the urethane acrylates in the media 1 to 5 are very suitable for the production of holographic media owing to the higher value for DE.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A urethane acrylate of the general Formula (I):

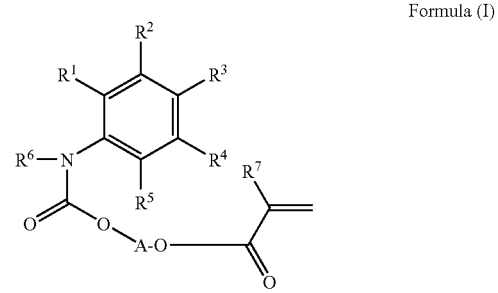

Formula (I)

wherein $R^1$, $R^2$, $R^3$, $R^4$ and $R^5$ each independently represent a substituent selected from the group consisting of hydrogen, halogens, $C_{1-6}$-alkyls, trifluoromethyl, $C_{1-6}$-alkylthios, $C_{1-6}$-alkylselenos, $C_{1-6}$-alkyltelluros, and nitro groups, with the proviso that at least one of $R^1$, $R^2$, $R^3$, $R^4$ and $R^5$ is not hydrogen;

$R^6$ and $R^7$ each independently represent a substituent selected from the group consisting of hydrogen and $C_{1-6}$-alkyls; and A represents a saturated or unsaturated, linear or branched $C_{1-6}$-alkyl radical or a polyalkylene oxide radical having 2-6 ethylene oxide or propylene oxide units;

wherein at least one of $R^1$, $R^2$, $R^3$, $R^4$ and $R^5$ represents a $C_{1-6}$-alkylthio substituent or chlorine or bromine.

2. The urethane acrylate according to claim 1, wherein $R^6$ and $R^7$ each represent a hydrogen atom.

3. The urethane acrylate according to claim 1, wherein A is a linear $C_2$-$C_4$ or branched $C_3$-alkyl radical.

4. A process for the preparation of urethane acrylates according to claim 1, the process comprising: reacting an isocyanate of the general Formula (II)

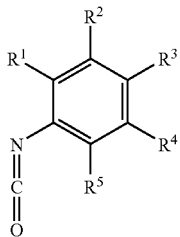

Formula (II)

with a compound of the general Formula (III)

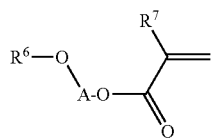

Formula (III)

wherein $R^1$, $R^2$, $R^3$, $R^4$ and $R^5$ each independently represent a substituent selected from the group consisting of hydrogen, halogens, $C_{1-6}$-alkyls, trifluoromethyl, $C_{1-6}$-alkylthios, $C_{1-6}$-alkylselenos, $C_{1-6}$-alkyltelluros, and nitro groups, with the proviso that at least one of $R^1$, $R^2$, $R^3$, $R^4$ and $R^5$ is not hydrogen;

$R^6$ represents hydrogen;

$R^7$ represents a substituent selected from the group consisting of hydrogen and $C_{1-6}$-alkyls; and A represents a saturated or unsaturated, linear or branched $C_{1-6}$-alkyl radical or a polyalkylene oxide radical having 2-6 ethylene oxide or propylene oxide units;

wherein at least one of $R^1$, $R^2$, $R^3$, $R^4$ and $R^5$ represents a $C_{1-6}$-alkylthio substituent or chlorine or bromine.

5. The process according to claim 4, wherein the isocyanate of the general Formula (II) comprises one or more isocyanates selected from the group consisting of 2-thiomethylphenyl isocyanate, 3-thiomethylphenyl isocyanate, 4-thiomethylphenyl isocyanate, 2-chlorophenyl isocyanate, 3-chlorophenyl isocyanate 4-chlorophenyl isocyanate, 2-bromophenyl isocyanate, 3-bromophenyl isocyanate, 4-bromophenyl isocyanate, and mixtures thereof.

6. The process according to claim 4, wherein the compound of the general Formula (III) comprises one or more compounds selected from the group consisting of 2-hydroxyethyl acrylate, 3-hydroxypropyl acrylate, 4-hydroxybutyl acrylate, polypropyleneoxide mono(meth)acrylates, polyethylene oxide mono(meth)acrylates, and mixtures thereof.

7. A holographic medium comprising a urethane acrylate according to claim 1.

8. A process comprising: providing a polymer matrix comprising a urethane acrylate according to claim 1; subjecting the polymer matrix to electromagnetic radiation such that the urethane acrylate is selectively polymerized.

9. A layer or molding comprising a urethane acrylate according to claim 1.

10. The layer or molding according to claim 9, wherein the layer or molding has a refractive index of >1.50 at 405 nm.

11. The layer or molding according to claim 9, wherein the layer or molding has a DE value, measured by means of two-beam interference in reflection arrangement, of >25%.

12. A holographic optical element/image prepared by the process according to claim 8.

13. An article selected from the group consisting of optical lenses, mirrors, deflection mirrors, filters, diffusion screens, diffraction elements, waveguides, light guides, projection screens, masks, personal portraits, biometric presentations in security documents, images, image structures and combinations thereof comprising a layer or molding according to claim 9.

* * * * *